(12) United States Patent
Behroozi

(10) Patent No.: US 8,474,306 B1
(45) Date of Patent: Jul. 2, 2013

(54) METHOD AND APPARATUS FOR MEASUREMENT OF FLUID PROPERTIES

(75) Inventor: Feredoon Behroozi, Cedar Falls, IA (US)

(73) Assignee: University of Northern Iowa Research Foundation, Cedar Rapids, IA (US)

( * ) Notice: Subject to any disclaimer, the term of this patent is extended or adjusted under 35 U.S.C. 154(b) by 334 days.

(21) Appl. No.: 12/788,613

(22) Filed: May 27, 2010

Related U.S. Application Data

(60) Provisional application No. 61/184,638, filed on Jun. 5, 2009.

(51) Int. Cl.
*G01N 13/00* (2006.01)

(52) U.S. Cl.
USPC ........................................ 73/64.52

(58) Field of Classification Search
USPC ................ 73/64.48, 64.52; 356/138
See application file for complete search history.

(56) References Cited

U.S. PATENT DOCUMENTS

| | | | |
|---|---|---|---|
| 3,618,374 A * | 11/1971 | Miller | 73/104 |
| 3,696,665 A * | 10/1972 | Poppe et al. | 73/104 |
| 4,050,822 A | 9/1977 | Grat | |
| 4,688,938 A | 8/1987 | Demoulin et al. | |
| 5,080,484 A | 1/1992 | Schneider et al. | |
| 5,115,677 A * | 5/1992 | Martin et al. | 73/64.48 |
| 7,952,698 B2 * | 5/2011 | Friedrich et al. | 356/138 |
| 2009/0081384 A1 * | 3/2009 | Plissonnier et al. | 427/578 |

OTHER PUBLICATIONS

Kusumaatmaja et al., "Modeling contact angle hysteresis on chemically patterned and superhydrophobic surfaces," Feb. 6, 2008.*
"Information on Contact Angle", as accessed online at http://www.ramehart.com/contactangle.htm on Jun. 20, 2012 (4 pages as printed).
Behroozi et al., "The Profile of a Dew Drop", American Journal of Physics, (1996) pp. 1120-1125, vol. 64.
Behroozi "Determination of contact angle from the maximum height of enlarged drops on solid surfaces", American Journal of Physics, (Apr. 2012) pp. 284-288 vol. 80, Issue 4.

* cited by examiner

*Primary Examiner* — John Fitzgerald
(74) *Attorney, Agent, or Firm* — Frederickson & Byron, P.A.

(57) ABSTRACT

A method and apparatus for determining the contact angle and/or surface tension of a liquid on a solid surface is described. The method involves placing a fluid drop on a solid surface, and gradually increasing its volume by adding more fluid, while continuing to determine the corresponding increase in fluid height, until the drop attains maximum height beyond which additional fluid only increases the drop footprint and not height, and determining the equilibrium height and in turn the contact angle by means of an equation that correlates contact angle with depth below the fluid surface, together with the fluid surface tension and liquid density. The method may in turn be used to determine the fluid surface tension from the equilibrium height when the contact angle and density of the fluid are known.

11 Claims, 3 Drawing Sheets

A large drop reaching its maximum height as indicated by the flat top.

Contact angle defined

A large drop reaching its maximum height as indicated by the flat top.

The profile of a large drop resting on a solid surface. The drop has reached its maximum height so the boundary line begins horizontally at top but turns downward as it descends.

The reflected laser light from the top of the patch forms a cone when the surface is not flat.

The reflected laser beam has the same diameter as the incident beam when the surface is flat.

The ring method for measuring the footprint area of the liquid. The liquid front is represented by the arc length L which is subtended by angle $\Phi$.

METHOD AND APPARATUS FOR MEASUREMENT OF FLUID PROPERTIES

CROSS-REFERENCE TO RELATED APPLICATION

The present application claims priority to U.S. Application No. 61/184,638, filed Jun. 5, 2009, the entire disclosure of which is incorporated herein by reference.

TECHNICAL FIELD

The present invention relates to scientific methods and apparatuses, and in particular, those used to determine fluid properties, including either the contact angle between a liquid and solid surface or the surface tension of the fluid itself.

BACKGROUND OF THE INVENTION

When a sample of fluid is placed on a solid substrate, the leading edge of the sample meets the solid surface at a precise angle, which is referred to as the contact angle. Technically, the contact angle is the angle between the liquid/solid interface and the liquid/vapor interface at the point of contact. The more exactly the contact angle can be measured, the more precisely the wetting properties of the sample fluid can be determined.

In current practice the contact angle is measured directly from the profile of a liquid droplet which is placed on a solid substrate. In the present state of the art, precise measurement of the contact angle is difficult because the angle between the solid surface and the tangent line at the contact point (FIG. 1) is subject to measurement errors. Any local roughness or surface contamination affects the angle. Furthermore, the measurement gives a different result for advancing or receding drops.

Various patents and other teachings address the measurement of contact angle between fluids and solids; most, if not all, tend to measure the angle directly by placing a droplet on the surface and then use some way to measure the angle. See, for instance, U.S. Pat. No. 5,268,733 (Issued Dec. 7, 1993) for "Method and Apparatus for Measuring Contact Angles of Liquid Droplets on Substrate Surfaces"; U.S. Pat. No. 5,080,484 (Issued Jan. 14, 1992) for "Method of Measuring the Contact Angle of Wetting Liquid on a Solid Surface"; U.S. Pat. No. 4,688,938 (issued Aug. 25, 1987) for "Method and Apparatus for Determining the Contact Angle of a Drop of Liquid Placed on Solid or Liquid Horizontal Substrate"; and U.S. Pat. No. 4,050,822 (issued Sep. 27, 1977) "Drop Measuring Apparatus, and a Method of Evaluating Materials Wettability".

The first contact angle measuring device, known as a goniometer, was designed by Dr. William Zisman of the Naval Research Laboratory in the early 1960's. The original contact angle goniometer used a special microscope to measure the contact angle of a drop from its profile. Modern instruments use digital cameras and software to capture and analyze the drop profile. Commercial goniometers have been made available for the last forty years, e.g., by Ramé-Hart Instrument Company, New Jersey, U.S.A., (http://www.rameheart.com/).

SUMMARY OF THE INVENTION

This invention embodies a new method for measuring the contact angle between a fluid and a solid surface. The most common method for measuring the contact angle is to place a droplet of fluid on the solid surface and measure the contact angle from the optical profile of the droplet by goniometry. The current invention uses a completely new method to determine the contact angle by measuring the maximum height of a patch of fluid resting on the solid surface.

Figure 1:
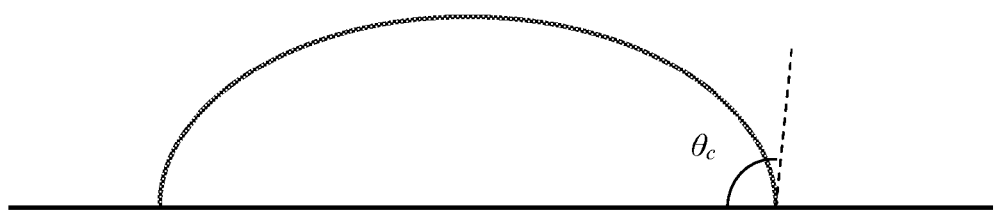
FIG. 1 depicts the profile of a drop on a flat surface, for use in defining contact angle.
Figure 2:
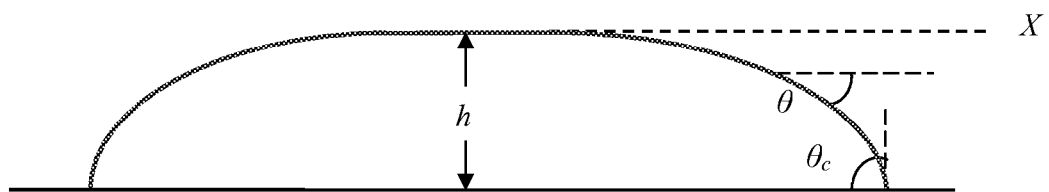
FIG. 2 depicts a drop reaching its maximum height as indicated by the flat top.

In one preferred embodiment, a drop of fluid is placed on the solid surface. The drop size is gradually increased by adding fluid until it attains its maximum height beyond which additional fluid only increases its footprint not its height (see FIG. 2). The liquid patch is then rolled gently on the substrate to attain its equilibrium height. Measurement of the equilibrium height yields the contact angle through a new equation. This method is far simpler than the direct measurement of the contact angle and produces consistent and reliable results because the maximum height of the drop is determined by the condition of the solid surface along the entire fluid-solid line of contact. Thus, the measurement gives a value for the contact angle which is characteristic of the global property of the surface and therefore largely unaffected by local surface defects. In a related aspect, the method can be used for determining the surface tension of a fluid as well, e.g., where the contact angle is known.

Given the description of the current invention, those skilled in the art will be able to determine the manner in which existing apparatuses and techniques can be used and adapted to accomplish the method described herein. For instance, conventional goniometers can be adapted or modified to provide the suitable hardware and/or corresponding software for performing a method of the present invention.

For instance, Rame-Hart currently sells a "Standard Goniometer (Model 200)" together with current version 2.1 of DROPimage Standard. The current software determines the contact angle from the profile of the drop by a fitting routine. In order to perform a preferred method of this invention, new or modified software can be provided in order to obtain the contact angle from a measurement of the maximum height of the fluid patch by using the mathematical equations provided in this invention.

In turn, the present invention includes as well an apparatus and corresponding software and/or computer adapted to perform some or all steps involved in a method of this invention.

DETAILED DESCRIPTION

Relation between the Contact Angle and the Liquid Height. Consider a layer of liquid with a free edge resting on a horizontal solid surface. The cross section of the free edge forms a line that begins at the horizontal liquid surface at the top of the layer and curves down to meet the solid surface at the contact angle $\theta_c$. The local curvature of this line is zero at the top but increases with depth below the horizontal liquid surface.

Figure 3:
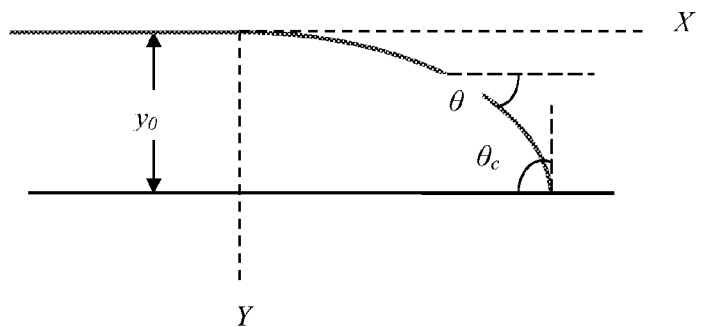
FIG. 3 depicts the profile of a large drop resting on a solid surface, the drop having reached its maximum height so that the boundary line begins horizontally at top but turns downward as it descends.

For analysis a rectangular coordinate system is used (see FIG. 3), where the x-axis runs along the horizontal liquid surface, and the y-axis is normal to it. Note that in this system y increases with depth and $\theta$ represents the angle between the liquid boundary line and the horizontal. The boundary line may be represented by a function y(x) whose derivative is given by tan $\theta$, $$dy/dx = \tan \theta. \quad (1)$$

Furthermore, the Young-Laplace relation provides a link between the local mean curvature at a point on the boundary line and its depth y below the fluid surface, $$\sigma(1/R_1 + 1/R_2) = \rho g y, \quad (2)$$

Here $R_1$ and $R_2$ are the two principal radii of curvature, $\sigma$ is the surface tension, $\rho$ is the liquid density, and g is the acceleration of gravity. However, in this geometry the boundary line of the liquid layer is characterized by just one principal radius of curvature R, since the second one lying in the horizontal plane is essentially infinity. Therefore, Eq. (2) may be simplified to, $$1/R = \alpha y, \quad (3)$$

where, $$\alpha = (\rho g / \sigma).$$

The arc length ds of an element of the boundary curve may be written as, $$ds = R d\theta. \quad (4)$$

Note that in light of Eq (3) R is a function of y. Now we note that ds may also be expressed in the rectangular coordinate system as $$ds = (dx^2 + dy^2)^{1/2} \quad (5)$$

Using Eqs. (3) and (5) in Eq. (4), we find the differential equation which relates an infinitesimal change in $\theta$ at a point along the boundary curve to infinitesimal changes of coordinates x, and y of that point.

$$\alpha y (dx^2 + dy^2)^{1/2} = d\theta, \quad (6)$$

Using Eq. (1) in Eq. (6), we have $$\alpha y dx (\tan^2 \theta + 1)^{1/2} = d\theta, \quad (7)$$

Note that since $$(\tan^2 \theta + 1)^{1/2} = 1/\cos \theta \quad (8)$$

We may simplify Eq. (7) further to get, $$\alpha y dx = \cos \theta d\theta \quad (9)$$

Equation (9) may be further simplified by using the equality (dx=dy/tan $\theta$) from Eq. (1), $$\alpha y dy = \sin \theta d\theta \quad (10)$$

Equation (10) may be integrated to give the angle $\theta$ at a point on the boundary curve as a function of the depth of that point y, $$\tfrac{1}{2}\alpha y^2 = 1 - \cos \theta. \quad (11)$$

Equation (11) may be used to obtain the contact angle $\theta_c$, when the depth of the fluid layer is known. In particular, if $y_0$ is the depth, then $$(\rho g / 2\sigma) y_0^2 = 1 - \cos \theta_c. \quad (12)$$

Equation (12) provides a convenient method for determining the contact angle by measuring the thickness of a fluid layer on a horizontal solid surface, in a particularly preferred embodiment, requiring only the need to provide fluid density, and its surface tension.

The proposed method is in essence a global measure of the contact angle for a given surface since the height of the liquid layer is determined by the global interaction of the solid with liquid.

Equation (12) gives the contact angle in terms of the height of the liquid layer $y_o$ and the surface tension of the fluid. More explicitly, $$\theta_c = \cos^{-1}[1 - (\rho g / 2\sigma) y_0^2] \quad (13)$$

To demonstrate the validity of this method, we obtained liquid height data on two different solid surfaces: Teflon, and Lucite. The test liquids were pure water and water covered by soap.

Pure water has a surface tension of 72 dyne/cm, and a density of 1 g/cm$^3$. For soapy water the surface tension drops to 30 dyne/cm, but the density remains at 1 g/cm$^3$.

Data was taken after the expanding drop had reached maximum height to determine the advancing contact angle. After this measurement, the surface was tilted slowly to allow the drop to roll gently on the surface and find its equilibrium footprint. This equilibrium height was measured to obtain the equilibrium contact angle. This procedure was repeated for all other measurements

| Data: | | |
|---|---|---|
| Water on Teflon: | $y_0$ = 4.9 mm [Advancing] | → $\theta_c$ = 130° |
| | $y_0$ = 4.7 mm [Equilibrium] | → $\theta_c$ = 120° |
| Soapy water on Teflon: | $y_0$ = 1.9 mm [Advancing] | → $\theta_c$ = 66° |
| | $y_0$ = 1.7 mm [Equilibrium] | → $\theta_c$ = 58° |
| Water on Lucite: | $y_0$ = 3.3 mm [Advancing] | → $\theta_c$ = 75° |
| | $y_0$ = 3.2 mm [Equilibrium] | → $\theta_c$ = 72° |
| Soapy water on Lucite: | $y_0$ = 1.0 mm [Equilibrium] | → $\theta_c$ = 33° |

For comparison, we give the experimental values of contact angle measured directly from the profile of drops [F. Behroozi, H. K. Macomber, J. A. Dostal, C. H. Behroozi, and B Lambert, "The Profile of a Dew Drop", *American Journal of Physics*, vol. 64, pp. 1120-1125 (1996).]

| | |
|---|---|
| Water on Teflon: = | 130° ± 5°, |
| Water on Lucite: = | 70° ± 2° |

In both cases the old measurements are very close to the new values. However, one should not expect identical results since drop-based measurement of contact angle depends on local surface conditions.

To support the solid surface a stable platform is preferably provided whose height is adjustable. Normally a level indicator is used to insure a horizontally level support surface. For added versatility this platform should allow rotation around the vertical axis (spherical coordinate $\phi$) and tilt with respect to the vertical axis (spherical coordinate $\theta$) to allow the normal line to the surface point in any direction ($\theta$, and $\phi$). When the normal line is vertical ($\theta$=0), the support surface is level.

The liquid can be dispensed, for instance, through a calibrated syringe dispenser placed conveniently above the platform. The dispenser is used to place a drop on the solid surface and to enlarge its size as its height is monitored. The maximum height is reached when adding more fluid does not change the height.

Figure 4:
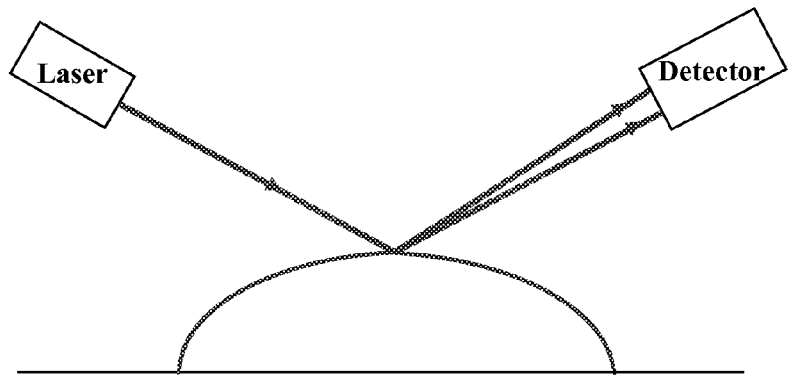
FIG. 4 depicts the profile of reflected laser light from the top of the patch forming a divergent beam when the surface is not flat.
Figure 5:
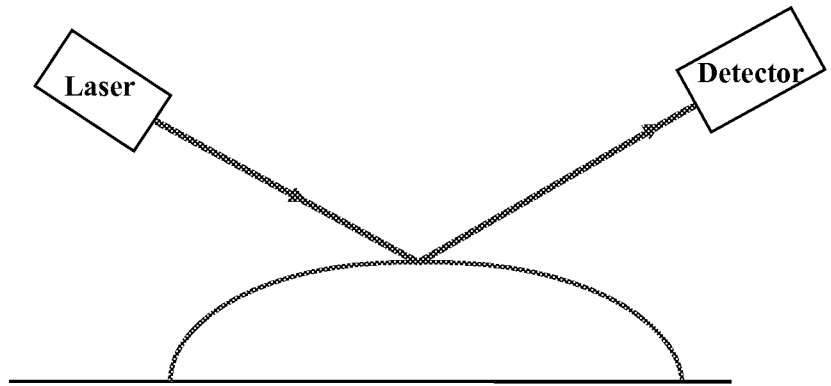
FIG. 5 depicts the profile of reflected laser light having the same diameter as the incident beam when the surface is flat.

Alternatively, the maximum height is reached when a flat region in the middle of the top surface of the fluid patch is detected, usual any suitable detection method or means. In a preferred embodiment, a laser beam is directed at a near-vertical angle of incidence unto the crown of the fluid as it is being enlarged. The reflected beam diverges when the fluid crown is curved (see FIG. 4). A flat surface is assured when the reflected beam shrinks to the same diameter as the incident beam (see FIG. 5).

Once the fluid patch has attained its maximum height, the patch is gently rolled back and forth by tilting the platform to allow the liquid to assume its equilibrium footprint.

A suitable imaging system, e.g., a high resolution CCD camera or any other suitable imaging system mounted so that its line of sight is parallel to the platform surface is used to obtain a high resolution record of the fluid height. For calibration the height of a standard 1 mm microscope slide is recorded under the same conditions.

The CCD image is transmitted through a suitable device, such as a digital video recorder PCI card (or through a VGA converter) to a computer for recording and analysis.

Other embodiments of the invention include measuring the height of the fluid by other common methods such as using a light beam to project an enlarged image, infrared ranging, laser ranging, or laser interferometry. A proportional area photo-detector placed behind the liquid patch may also be used to provide a signal to measure the height.

The height of the fluid layer may also be measured by simply dividing the known volume of the dispensed fluid by its footprint area. This method requires measurement of the surface area covered by the fluid which may be accomplished using any suitable method or means, e.g., by taking a high resolution image of the fluid patch from above. An alternative method for measurement of the liquid footprint is to place a circular Teflon ring (with inner radius R of about 2 cm, thickness of about 3 mm, and height of about 5 mm) on the surface of interest. A calibrated dispenser is used to place a large drop of liquid inside the ring and touching the left side of the ring. The drop is now enlarged by adding more liquid and causing the leading edge to advance to the right. As the liquid front advances, its horizontal curvature moderates until it transforms to a straight line (see FIG. 6).

Figure 6:
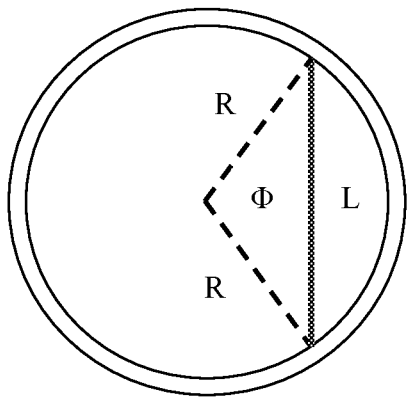
FIG. 6 depicts the ring method for measuring the footprint area of the liquid, where the liquid front is represented by the cord length L which is subtended by angle $\Phi$.

Referring to FIG. 6, if L is the cord representing the final length of the liquid front, and $\Phi$ is the angle subtending the cord, then simple geometry gives, $$\Phi = 2\sin^{-1}(L/2R).$$

The footprint of the liquid is given by, $$\text{Liquid Footprint} = \pi R^2 - \frac{1}{2} R^2 (\Phi - \sin \Phi)$$

Dividing the volume of the liquid by this area gives the height of the liquid. However, this method provides reliable height data only when corrections are applied to account for the curvature of the fluid boundary walls.

A further application of this method is the measurement of surface tension of fluids when the contact angle is known from other measurements. In this application the measurement of the height of the fluid patch gives the surface tension through Eq. (12) which may be recast as:

$$\sigma = (y_0^2 \rho g)/[2(1-\cos\theta_c)] \quad (14)$$

The results of the liquid height measurement on solid surfaces show unequivocally that the proposed method yields contact angle data that are in good agreement with direct measurements of the contact angle by profile goniometry. Furthermore, the method constitutes a much more convenient and reliable method for measuring the contact angle. The convenience is due to relative ease of measuring the height of the fluid layer by simple profiling, laser ranging, or other common methods of measuring small distances. The reliability is due to the fact that the method provides a global average of the contact angle along the line of contact all the way around the layer. Consequently, local rough spots or surface defects do not significantly affect the measurement.

In yet another aspect, the present invention provides an apparatus for determining the contact angle and/or surface tension of a liquid. Those skilled in the art, given the present description, will be able to determine the manner in which existing equipment can be used or retrofitted, e.g., by the provision of a convenient means to measure the height of the liquid layer and the corresponding analytical software, in order to accomplish the method of this invention.

In one particularly preferred embodiment, for instance, the apparatus comprises:

a) a solid platform with fine height and tilt adjustments, b) freedom to rotate the platform around the vertical axis (spherical coordinate angle $\phi$) and tilt with respect to the vertical axis (spherical coordinate angle $\theta$) to allow the normal line to the surface point in any desired orientation ($\theta$, and $\phi$), c) a level indicator to ensure a horizontal surface when the normal to the platform is vertical ($\theta=0$), d) a calibrated syringe dispenser held above the platform to dispense a fluid drop onto the solid surface and enlarge its size to assure a flat top in the middle of the fluid patch, e) controlled tilting of the platform by $\theta = \pm 10°$ at any $\phi$ to allow the liquid patch to roll around to assume its equilibrium footprint, f) a high resolution CCD camera mounted on a separate and adjustable platform with its line of sight parallel to the platform surface, g) a standard and finely calibrated ruler placed vertically on the platform and near the fluid patch for calibration, and h) CCD image transfer through a suitable device, such as a digital video recorder PCI card (or through a VGA converter) to a computer for recording and analysis.

In turn, the method of this invention can include measuring the height of the fluid placed on the platform of such an apparatus, by using other common methods such as projection of an enlarged image, infrared ranging, laser ranging, shadow-based detection by a photo-sensor, and laser interferometry.

Further, the method of this invention can include monitoring the surface curvature of the crown of the liquid patch by light reflection while the patch is enlarged. The patch reaches its maximum height when the top surface attains zero curvature.

Further, the method of this invention can include monitoring the surface curvature of the crown of the liquid patch by directing a laser beam at a near-vertical angle of incidence unto the crown as it is being enlarged. The reflected beam shrinks to the same diameter as the incident beam when a flat surface appears as described herein.

Similarly, the method can include measuring the height of the fluid layer by dividing the known volume of the dispensed fluid by its footprint area. This method requires measurement of the surface area covered by the fluid which is obtained from a high resolution calibrated image of the fluid patch taken in the manner described herein.

Similarly, the method can include measurement of the liquid footprint by using a Teflon ring in the manner described herein. Dividing the fluid volume by the footprint provides the height of the fluid as described herein.

In one preferred embodiment, a method of this invention further comprises measuring the advancing contact angle by adding more fluid after the patch has attained its maximum equilibrium height.

In another preferred embodiment, the method further comprises measuring the receding contact angle by first adding more fluid after the patch has attained its equilibrium maximum height, then removing some fluid.

In yet another preferred embodiment, the method further comprises measuring the height of the fluid layer by dividing the known volume of the dispensed fluid by its footprint area. Such a method can be performed in any suitable manner, for instance:

a) by placing a suitable (e.g., Teflon brand) ring having a suitable inner radius R (e.g., between about 1.5 and about 3 cm), suitable thickness (e.g., between about 2 mm and about 3 mm), and suitable height (e.g., between about 4 mm and about 6 mm), on the surface of interest, b) using a calibrated dispenser to place a large drop of liquid inside the ring and touching one side, c) enlarging the liquid patch by adding more liquid and causing the leading edge to advance (as the liquid front advances, its convex curvature moderates until it transforms to a straight line), d) whereby the footprint of the liquid is given by, $$\text{Footprint Area} = \pi R^2 - \frac{1}{2}R^2(\Phi - \sin \Phi)$$

where, $\Phi$ is the angle subtended by the cord representing the liquid front, and e) obtaining the height of the liquid by dividing the liquid volume by its foot print area.

In another preferred embodiment, the method of this invention comprises measuring the surface area covered by the fluid which is obtained from a high resolution calibrated image of the fluid patch.

In yet another preferred embodiment, the method comprises monitoring the curvature of the crown area of the liquid patch by light reflection to ascertain its flatness by a method comprising of:

a) directing a laser beam to strike the crown of the liquid patch at near vertical angle, b) monitoring the diameter of the reflected beam as the liquid patch is gradually enlarged, c) assuring flatness of the top surface when the diameter of the reflected beam is the same as the diameter of the incident beam.

The present invention further provides a method to obtain the surface tension of fluids when the contact angle is known. In this embodiment the height of the fluid patch measured by method of this invention gives the surface tension through Eq. (14):

$$\sigma = (y_0^2 \rho g)/[2(1 - \cos \theta_c)]$$

Finally, the present invention provides a computer program for instructing a computer to perform a method as described herein, as well as a computer readable medium that comprises such a computer program. The invention further provides a goniometer adapted for use in performing a method of this invention, e.g., by providing instructions for use in this regard, and/or by providing one or more modifications to a conventional goniometer, such modifications (e.g., control software) adapted to permit its use in performing the method described herein.

What is claimed is:

1. A method for determining contact angle of a liquid, comprising the steps of
    a) placing a fluid drop on a solid horizontal surface,
    b) gradually increasing the volume of the fluid drop, while continuing to determine the corresponding increase in fluid height, until the drop attains maximum height beyond which additional fluid only increases the drop footprint and not its height,
    c) determining the equilibrium height and in turn the contact angle by means of the following equation:

$$\theta_c = \cos^{-1}[1 - (\rho g/2\sigma)y_0^2]$$

where
$\theta_c$ is the contact angle,
$y_0$ is the depth below the fluid surface,
$\sigma$ is the surface tension, and
$\rho$ is the liquid density.

2. A method according to claim 1, further comprising measuring the advancing contact angle by adding more fluid after the patch has attained its maximum equilibrium height.

3. A method according to claim 1, further comprising measuring the receding contact angle by first adding more fluid after the patch has attained its equilibrium maximum height, then removing some fluid.

4. A method according to claim 1, further comprising measuring the height of the fluid layer by dividing the known volume of the dispensed fluid by its footprint area consisting of:
    a) placing a ring having suitable inner radius R, thickness, and height, on the surface of interest,
    b) using a calibrated dispenser to place a large drop of liquid inside the ring and touching one side,
    c) enlarging the liquid patch by adding more liquid and causing the leading edge to advance, As the liquid front advances, its convex curvature moderates until it transforms to a straight line,
    d) whereby the footprint of the liquid is given by, $$\text{Footprint Area} = \pi R^2 - \frac{1}{2}R^2(\Phi - \sin \Phi)$$

where,
$\Phi$ is the angle subtended by the cord representing the liquid front, and
    e) obtaining the height of the liquid by dividing the liquid volume by its foot print area.

5. A method according to claim 1, further comprising measuring the surface area covered by the fluid which is obtained from a high resolution calibrated image of the fluid patch.

6. A method according to claim 1, further comprising monitoring the curvature of the crown area of the liquid patch by light reflection to ascertain its flatness by a method comprising of:
    a) directing a laser beam to strike the crown of the liquid patch at near vertical angle,
    b) monitoring the diameter of the reflected beam as the liquid patch is gradually enlarged,
    c) flatness of the top surface is assured when the diameter of the reflected beam is the same as the diameter of the incident beam.

7. A method according to claim 1, further comprising the step of obtaining the surface tension of a fluid when the contact angle is known, the method comprising measuring the height of the fluid patch, to provide the surface tension through the following equation:

$$\sigma = (y_0^2 \rho g)/[2(1-\cos\theta_c)].$$

8. An apparatus for determining the contact angle or surface tension of a liquid, the apparatus comprising components and corresponding controls for determining the variables needed to perform a method that comprises the steps of:
   a) placing a fluid drop on a solid horizontal surface,
   b) gradually increasing the volume of the fluid drop, while continuing to determine the corresponding increase in fluid height, until the drop attains maximum height beyond which additional fluid only increases the drop footprint and not its height,
   c) determining the equilibrium height and in turn the contact angle by means of the following equation:

$$\theta_c = \cos^{-1}[1-(\rho g/2\sigma)y_0^2]$$

where
$\theta_c$ is the contact angle,
$y_0$ is the depth below the fluid surface,
$\sigma$ is the surface tension, and
$\rho$ is the liquid density.

9. An apparatus according to claim 8, wherein the apparatus comprises one or more features selected from the group consisting of:
   a) a solid platform with fine height and tilt adjustments,
   b) freedom to rotate the platform around the vertical axis (spherical coordinate angle $\phi$) and tilt with respect to the vertical axis (spherical coordinate angle $\theta$) to allow the normal line to the surface point in any desired orientation ($\theta$, and $\phi$),
   c) a level indicator to ensure a horizontal surface when the normal to the platform is vertical ($\theta=0$),
   d) a calibrated syringe dispenser held above the platform to dispense a fluid drop onto the solid surface and enlarge its size to assure a flat top in the middle of the fluid patch,
   e) controlled tilting of the platform by $\theta=\pm10°$ at any $\phi$ to allow the liquid patch to roll around to assume its equilibrium footprint,
   f) a high resolution CCD camera mounted on a separate and adjustable platform with its line of sight parallel to the platform surface,
   g) a standard and finely calibrated ruler placed vertically on the platform and near the fluid patch for height calibration, and
   h) CCD image transfer through a suitable device to a computer for recording and analysis.

10. An apparatus according to claim 9, wherein the apparatus comprises each of the features a) through h).

11. An apparatus according to claim 9, wherein the apparatus provides for measuring the height of the fluid placed on the platform of the apparatus using a method selected from the group consisting of an enlarged image, infrared ranging, laser ranging, shadow-based detection by a photo-sensor, and laser interferometry.

* * * * *